US009788887B2

(12) United States Patent
Ellman et al.

(10) Patent No.: US 9,788,887 B2
(45) Date of Patent: Oct. 17, 2017

(54) SURGICAL TOOL AND METHOD HAVING MULTIPLE ELECTRODES

(71) Applicant: ELLIQUENCE, Baldwin, NY (US)

(72) Inventors: Alan G Ellman, Hewlett, NY (US);
Meindert Stek, Saratoga, CA (US);
John Pikramenos, Astoria, NY (US);
Scott Goldsmith, Woodmere, NY (US);
Paul Buhrke, Garden City, NY (US);
Spencer Ellman, New York, NY (US);
Ellman Ian, New York, NY (US)

(*) Notice: Subject to any disclaimer, the term of this patent is extended or adjusted under 35 U.S.C. 154(b) by 350 days.

(21) Appl. No.: 14/627,381

(22) Filed: Feb. 20, 2015

(65) Prior Publication Data
US 2016/0242837 A1    Aug. 25, 2016

(51) Int. Cl.
*A61B 18/14* (2006.01)
*A61B 18/00* (2006.01)
*A61B 18/12* (2006.01)

(52) U.S. Cl.
CPC ...... *A61B 18/1477* (2013.01); *A61B 18/1206* (2013.01); *A61B 18/1402* (2013.01); *A61B 2018/00607* (2013.01); *A61B 2018/126* (2013.01); *A61B 2018/1253* (2013.01); *A61B 2018/143* (2013.01); *A61B 2018/1415* (2013.01); *A61B 2018/1427* (2013.01); *A61B 2018/1467* (2013.01)

(58) Field of Classification Search
CPC ............ A61B 18/1206; A61B 18/1402; A61B 18/1477; A61B 2018/00607; A61B 2018/1253; A61B 2018/126; A61B 2018/1415; A61B 2018/1427; A61B 2018/143; A61B 2018/1467
See application file for complete search history.

(56) References Cited

U.S. PATENT DOCUMENTS

| | | | | |
|---|---|---|---|---|
| 6,030,384 A * | 2/2000 | Nezhat | ............... | A61B 18/1442 606/48 |
| 6,440,121 B1 * | 8/2002 | Weber | .................. | A61B 18/24 606/13 |
| 2006/0047281 A1 * | 3/2006 | Kreindel | ............... | A61B 18/14 606/49 |
| 2009/0105706 A1 * | 4/2009 | Livneh | ............... | A61B 18/1477 606/33 |
| 2012/0046658 A1 * | 2/2012 | Kreindel | ............ | A61B 18/1477 606/41 |
| 2012/0185029 A1 * | 7/2012 | Flyash | .................. | A61B 18/14 607/148 |
| 2013/0282085 A1 * | 10/2013 | Lischinsky | ........ | A61B 18/1206 607/102 |
| 2015/0359585 A1 * | 12/2015 | Weber | ............... | A61B 18/1402 606/49 |

* cited by examiner

*Primary Examiner* — Michael Peffley

(57) ABSTRACT

An electrosurgical device that has a head having a face. A handle connectable to an RF generator. The device has a plurality of teeth extending from the face. At least one of the plurality of teeth as a first electrical charge. A second of the plurality of teeth has a second electrical charge.

4 Claims, 10 Drawing Sheets

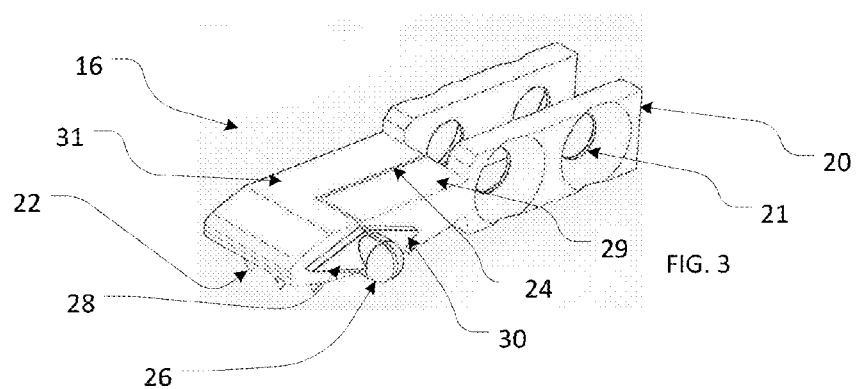
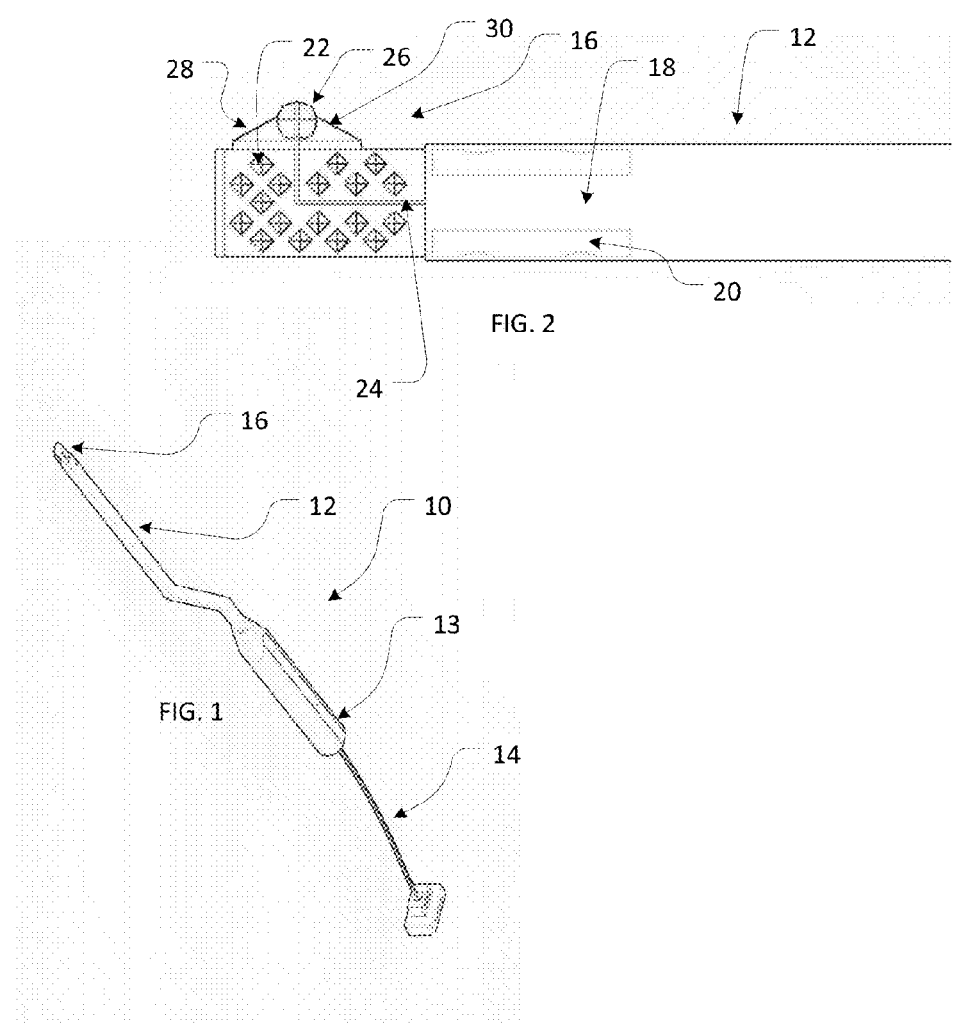

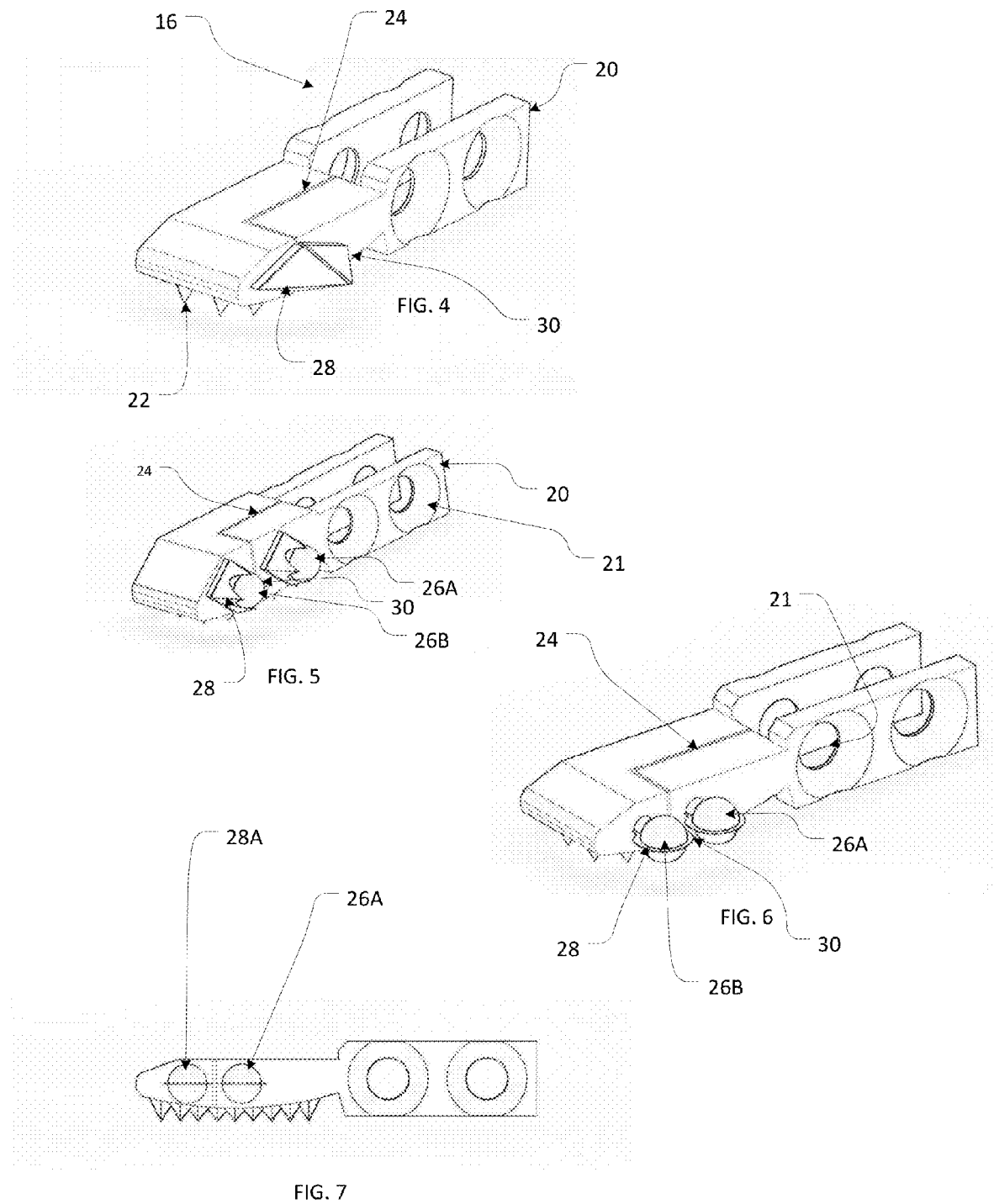

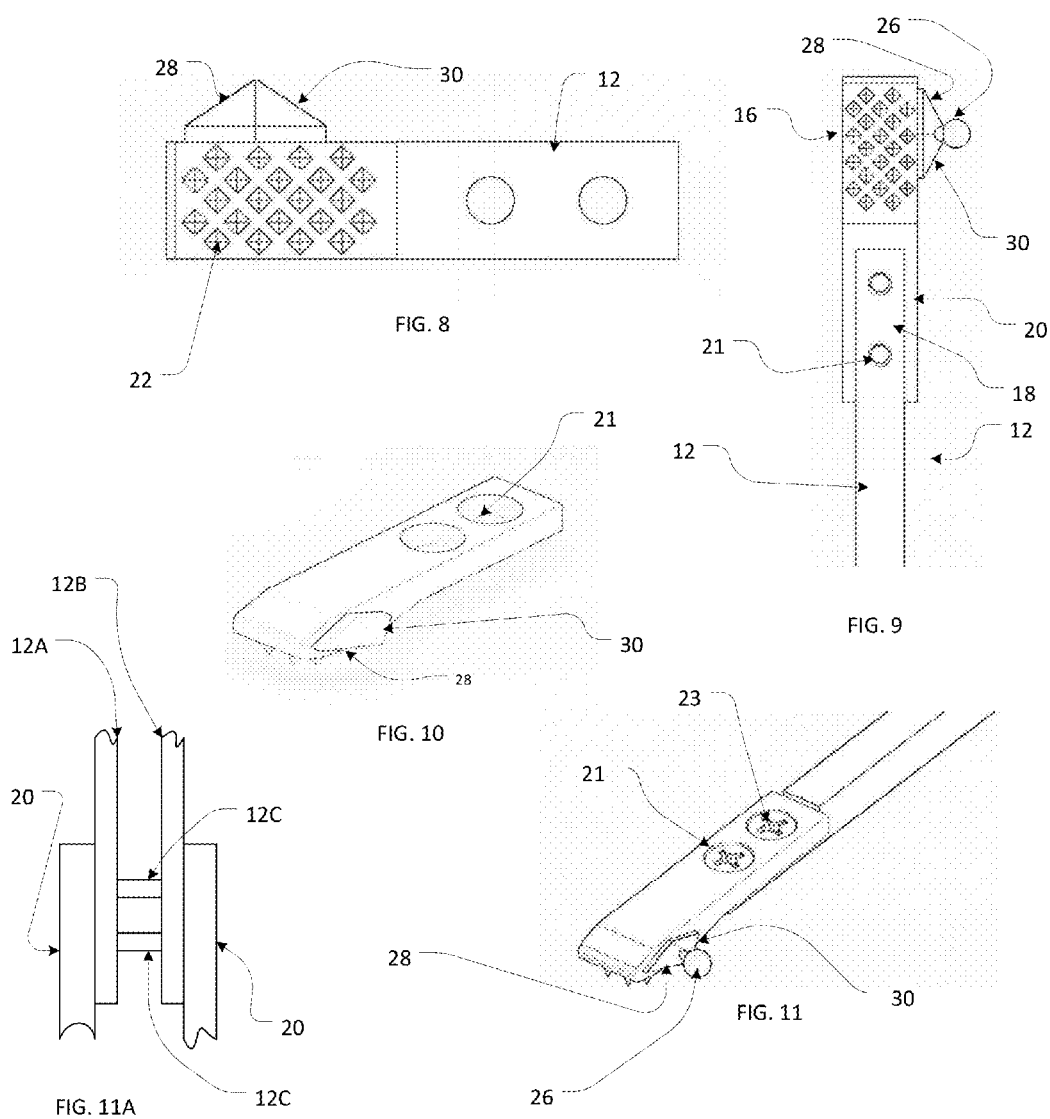

SURGICAL TOOL AND METHOD HAVING MULTIPLE ELECTRODES

CROSS REFERENCE TO RELATED APPLICATIONS

The present application claims priority to U.S. provisional application Ser. No. 61/942,953 titled "Surgical Tool and Method," filed on Feb. 20, 2014 and 61/946,678 titled "Surgical Tool and Method," filed on Feb. 28, 2014 wherein the contents of the above mentioned applications are hereby incorporated by reference in their entirety.

BACKGROUND OF THE INVENTION

The present invention relates to surgery performed on a patient by a surgical physician, a surgeon, and, more specifically, relates to back surgery. Specialized back surgery on or in-between vertebrae of the spine and on spinal discs involves various meticulous surgical procedures which can be challenging, even for experienced surgeons who specialize in this particular surgery. Minimally invasive techniques are preferred over traditional open surgical procedures which require extensive operating time and post-operative recovery time.

When employing minimally invasive surgical techniques on or between spinal vertebrae or on discs, one of the challenging requirements relates to providing electrodes of an electrosurgical device into the operative field. For example, in one instance, the operative area between spinal vertebrae must be opened. The area between the vertebrae are then polished or abraded to prepare the surface for an implant. Accordingly, it is desirable to have a surgical instrument that is adapted to assist in conducting this procedure.

SUMMARY OF THE INVENTION

An electrosurgical device that has a head having a face. A handle connectable to an RF generator. The device has a plurality of teeth extending from the face. At least one of the plurality of teeth as a first electrical charge. A second of the plurality of teeth has a second electrical charge.

BRIEF DESCRIPTION OF THE DRAWINGS

FIG. 1 is a perspective view of a surgical tool according to an aspect of the invention;

FIG. 2 is a side view of a surgical tool according to an aspect of the invention;

FIG. 3 is a perspective view of a portion of a surgical tool according to an aspect of the invention;

FIG. 4 is a perspective view of a portion of a surgical tool according to an aspect of the invention;

FIG. 5 is a perspective view of a portion of a surgical tool according to an aspect of the invention;

FIG. 6 is a perspective view of a portion of a surgical tool according to an aspect of the invention;

FIG. 7 is a side view of the portion of a surgical tool according to an aspect of the invention;

FIG. 8 is a side view of a portion of a surgical tool according to an aspect of the invention;

FIG. 9 is a side view of a portion of a surgical tool according to an aspect of the invention;

FIG. 10 is a perspective view of a portion of a surgical tool according to an aspect of the invention;

FIG. 11 is a perspective view of a portion of a surgical tool according to an aspect of the invention;

FIG. 11A is a plan view of a portion of a surgical tool according to an aspect of the invention;

DETAILED DESCRIPTION OF PREFERRED EMBODIMENTS

Figure 12:
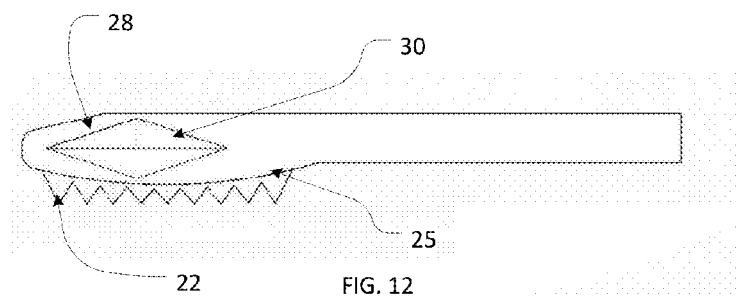
FIG. 12 is a side view of a portion of a surgical tool according to an aspect of the invention.

Referring now to FIG. 1, an embodiment of the invention is shown and described. In FIG. 1, a surgical device 10 is shown having a cable 14 connecting to a power source (see for example U.S. Pat. No. 7,674,261 the entirety of which is incorporated herein by reference). The surgical device 10 further has a handle 13 connecting at one axial end to the cable 14 and at the other axial end to an electrode 12. The electrode 12 includes bent portions that are bent at various locations as shown. One skilled in the art will recognize that other configurations of the electrode 12, such as being bent at different locations, are contemplated in the present embodiment.

At a distal end of the electrode 12 with respect to the handle 14 is located head 16. Referring now to FIG. 2 and FIG. 3, a bipolar configuration of a head 16 is shown and described in greater detail. Head 16 is engaged with component 18 of the electrode 12 through a receiver 20 incorporated into head 16. In one example, the component 18 is a pair of rectangles 12A and 12B that slides between the pair of receivers 20 (see FIG. 11A). The rectangles 12A and 12B of component 18 has apertures therethrough that align with bolt holes 21 such that bolts 12C can pass therethrough and connect head 16 with component 18. In one aspect, rectangle 12A as a different charge than rectangle 12B to provide different electrical charges or a bipolar charge relationship between different areas of the head 16 for reasons that will be described in greater detail. As will be understood, bolts or other fastening means are passed through bolt holes 21 and apertures in the component 18 to attach head 16 to electrode 12.

With continued reference to FIG. 2 and FIG. 3, head 16 generally includes a first portion 29 and a second portion 31. First portion 29 and second portion 31 are separated by dielectric region 24 that insulates first portion 29 from second portion 31. Electrical connections provided through the surgical device 16 provide electrical signals to and from first portion 29 and second portion 31 respectively (see FIGS. 24 and 25 for examples).

Teeth 22 protrude from a face of head 16 and are distributed across both first portion 29 and second portion 31. The teeth may have different configurations and, in one example, are generally diamond shaped, terminating at a point, and spaced from one another. Extending from a side region of head 16 is exposed electrode 26 surrounded by forward blade 28 and rearward blade 30. Exposed electrode 26, in the present embodiment, is semi-spherical with dielectric region 24 separating hemispherical exposed electrode 26 to quarter spheres. Forward blade 28 extends from one side of exposed electrode 26 and on one side of dielectric region 24 while rearward blade 30 extends from the opposite side of exposed electrode 26 and dielectric region 24. Accordingly, in one aspect, when the surgical devices moved in a forward direction, forward blade 28 can begin an incision followed by the exposed electrode 26 entering the incised area. Likewise, movement of the surgical tool in the opposite direction will yield rearward blade 30 entering the incised area followed by the exposed electrode 26. Forward blade 28 and rearward blade 30 can either be electrically connected to first portion 29 and second portion 31 such that they also transmit the electrosurgical currents to the incised area, or they may be insulated from first portion 29 and second portion 31 as well as exposed electrode 26 such that exposed electrode 26 provides and not the blades provide electrosurgical currents to the incised area.

Referring now to FIG. 4, another embodiment of the present invention is shown and described. In FIG. 4, exposed electrode 26 is omitted and what remains is forward blade 28 and rearward blades 30. Referring to FIG. 5, exposed electrode 26 includes a forward exposed electrode 26B and a rearward exposed electrode 26A. Each of such exposed electrodes include respectively forward blade 28 and rearward blade 30. As shown in the figure, each of the respective exposed electrodes and corresponding blades are located in respective ones of the portion 29 and portion 31. As will be described in greater detail, electrical signals provided through the surgical tool 16 are transmitted from one exposed electrode 26A to the other exposed electrode 26B.

Referring now to FIG. 6, another embodiment of the invention is shown and described. Here, forward exposed electrode 26B and rearward exposed electrode 26A are shown generally as spheres that include flat annular rings disposed thereabout to define forward blade 28 and rearward blade 30. FIG. 7 shows a side view of that described with respect to FIG. 6.

Figure 13:
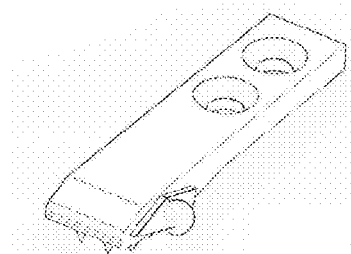
FIG. 13 is a perspective view of a portion of a surgical tool according to an aspect of the invention.
Figure 14:
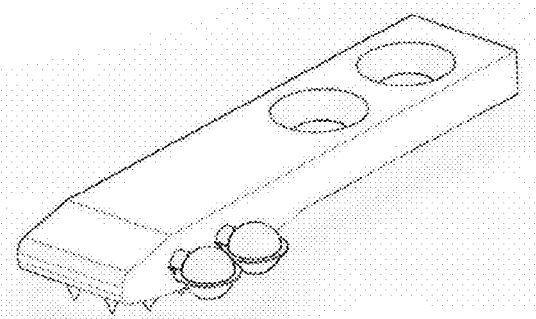
FIG. 14 is a perspective view of a portion of a surgical tool according to an aspect of the invention.
Figure 15:
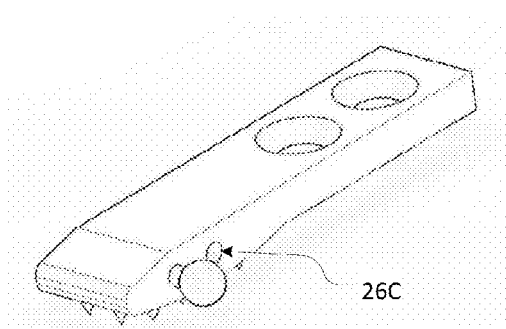
FIG. 15 is a perspective view of a portion of a surgical tool according to an aspect of the invention.
Figure 16:
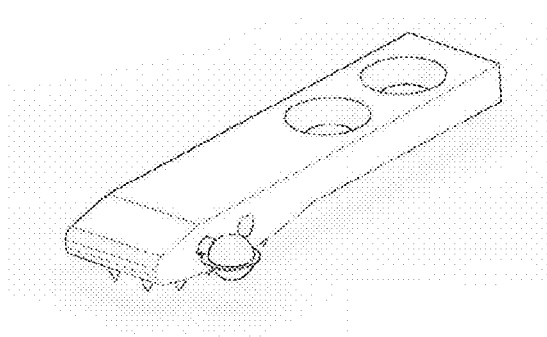
FIG. 16 is a perspective view of a portion of a surgical tool according to an aspect of the invention.

With reference to FIG. 9, another embodiment of the present invention is shown described. In FIG. 9, a monopolar configuration of head 16 is described. In this configuration, and electrical signal is provided through the electrode 12, through the head 16 and into the patient (as will be described). FIGS. 8, 10 and 11 show additional views. With reference to FIGS. 12, 13, 14 embodiments similar to those of previously discussed figures are shown except that in the present embodiment, the configurations are monopolar. FIG. 15 illustrates the head 16 with one of the exposed electrodes removed where aperture 26C is located.

Figure 17:
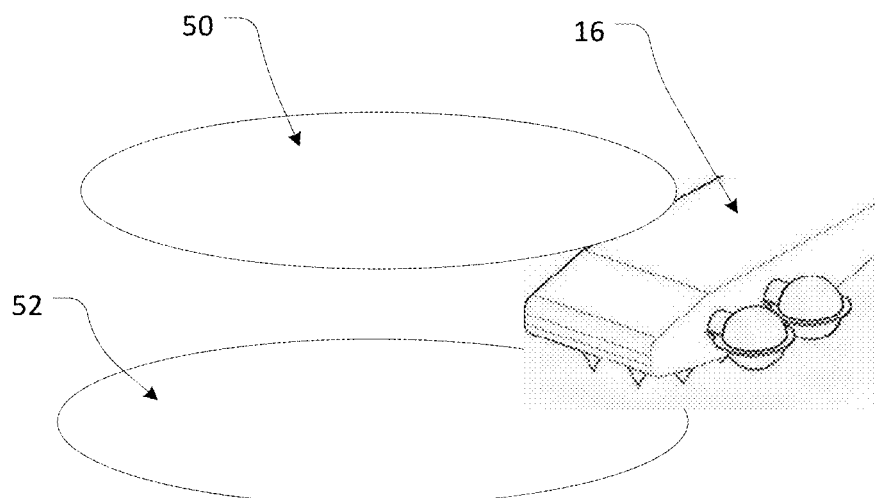
FIG. 17 is an operational view employing a surgical tool according to an aspect of the invention.
Figure 18:
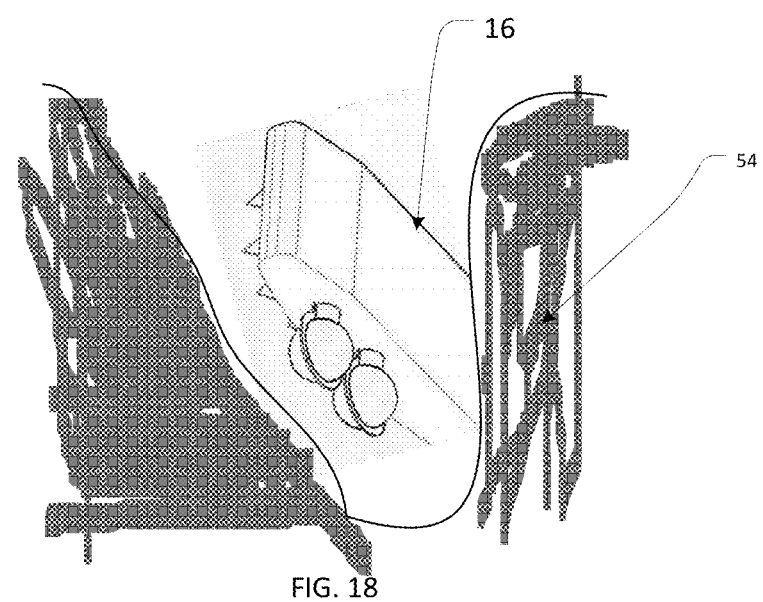
FIG. 18 is an operational view employing a surgical tool according to an aspect of the invention.

Referring now to FIGS. 17 and 18, the operation of an embodiment of the present invention is described. In FIG. 17, a surgeon is undertaking disc replacement in a spinal surgical procedure. In this procedure, the surgeon is inserting head 16 in between upper disc 50 and lower disc 52 in a patient's spine to remove damaged tissue therebetween with the use of a surgical tool 16. In this procedure, teeth 22 are abraded against the surface of disc 52 to initiate a healing response by the patient's body and thereby promote bone growth in the region to be repaired. In the monopolar configuration as described with respect to FIGS. 8 through 11, the electrical signal is transmitted from teeth 22 into lower disc 52. It will be understood that teeth 22 will be abraded against upper disc 50 or other regions in the patient's spinal region to initiate the aforementioned healing response. In a bipolar configuration, the electrical signal is transmitted from portion 29 through the lower disc 52 and into the portion 31. In the monopolar or bipolar configuration, the electrical signal assists in abrading the respective disc to initiate the healing response from the patient. One example of such monpolar or bipolar electrical current provision may be found in U.S. Pat. No. 7,101,370 the entirety of which is incorporated herein by reference.

With continued reference to the figures and specifically FIG. 18, the exposed electrodes and corresponding forward blade 28 and rearward blade 30 may be used for cutting damaged tissue such as tissue 54 from the region or coagulation or other desirable result in which the implant is to be positioned. In the configuration such as the bipolar configurations of FIG. 4, FIG. 5 and FIG. 6, the electrical signal is passed from rearward exposed electrode 26A to forward exposed electrode 26B. In the configuration such as FIG. 4, the absence of the exposed electrode 26 may result in superior cutting results. Likewise, where exposed electrodes 26 are provided and smaller forward blade 28 and rearward blade 30 are provided, a superior coagulation result may occur.

Figure 19:
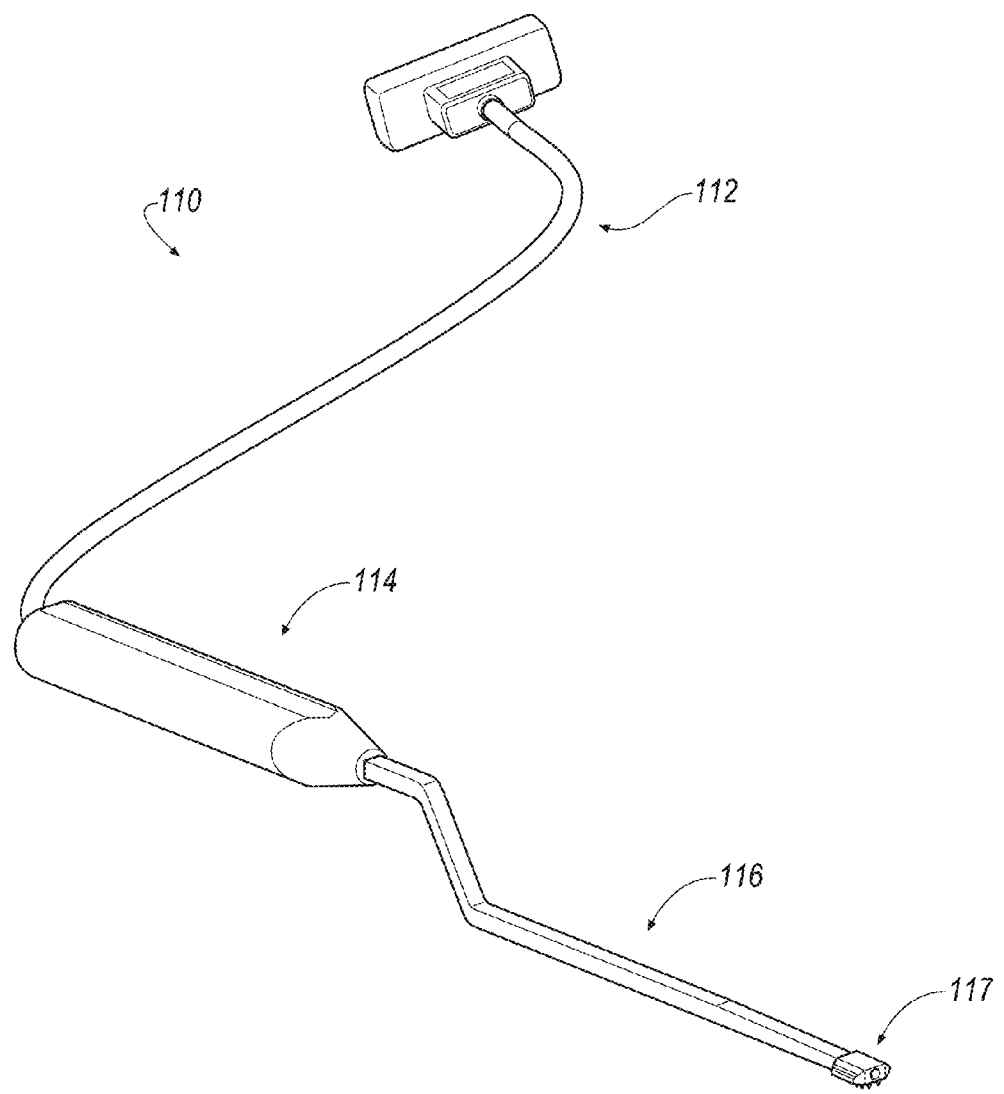
FIG. 19 is a perspective view of a surgical tool according to an aspect of the invention.

Referring now to FIG. 19, another embodiment of the invention is shown and described. In FIG. 19, a surgical device 110 is shown having a cable 112 connecting to a power source (see for example U.S. Pat. No. 7,674,261 the entirety of which is incorporated herein by reference). The surgical device 110 further has a handle 114 connecting at one axial end to the cable 112 and at the other axial end to an electrode 116. The electrode 116 includes bent portions that are bent at various locations as shown. One skilled in the art will recognize that other configurations of the electrode 116, such as being bent at different locations, are contemplated in the present embodiment. At a distal end of the electrode 116 with respect to the handle 114 is located head 117.

Figure 20:
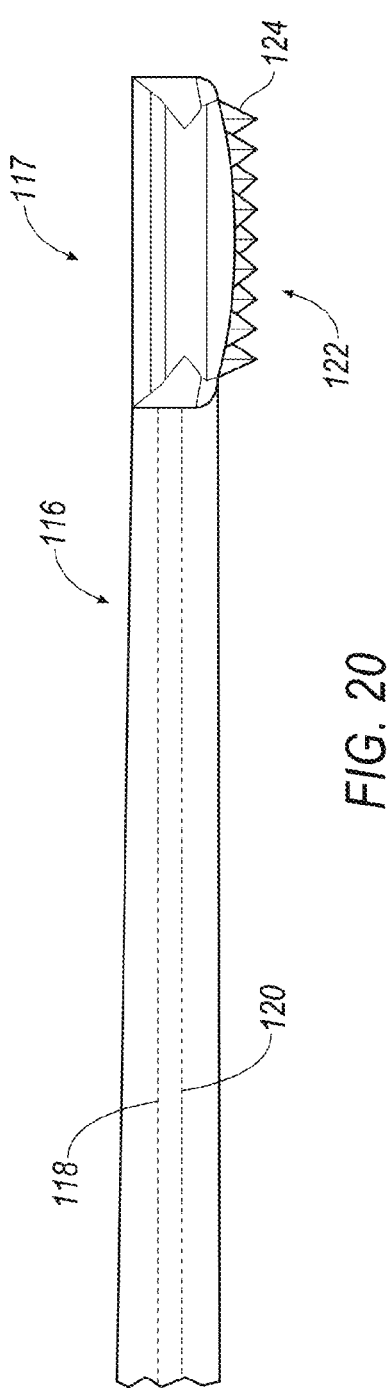
FIG. 20 is a side view of a surgical tool according to an aspect of the invention.

Referring now to FIG. 20, electrode 116 is shown in greater detail. Electrode 116 includes conductor 118 and conductor 120. Conductor 118 and conductor 120 may be in the form of wires, electrodes or other conductive regions. It will be understood that conductor 118 and conductor 120 provide an electrical signal from the power source (RF generator) through the cable 112, handle 114 and to the head 117. It will also be understood that depending on whether a monopolar or a bipolar configuration is desired (see for example the above referenced patent Incorporated herein by reference), only one conductor 118 may be used for a monopolar configuration while two conductors 118 and 120 may be used for a bipolar configuration.

With continued reference to FIG. 20 and with respect to a monopolar configuration, head 117 includes a face 122 having teeth 124 extending therefrom. In the monopolar configuration, conductor 118 provides an electrical signal to head 117 which is then transmitted through the teeth 124 to a patient and then to an external ground.

Figure 21:
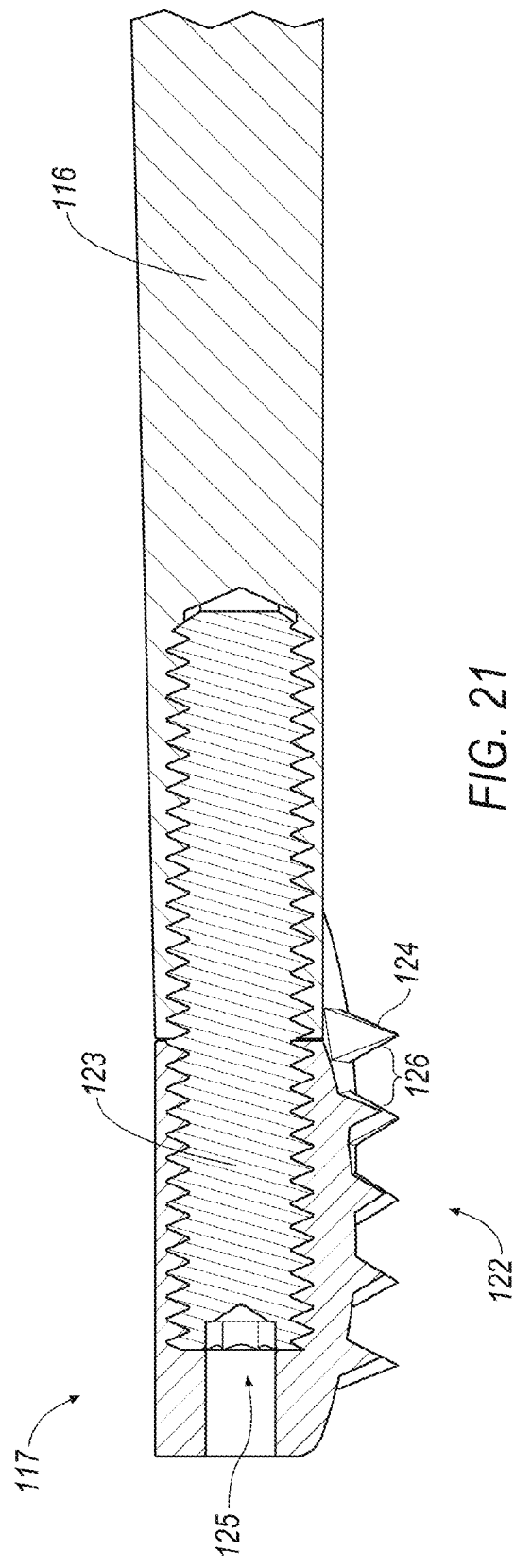
FIG. 21 is a side view of a surgical tool according to an aspect of the invention.

Referring now to FIG. 21, one embodiment of the assembly of the present invention is shown and described. In FIG. 21, all thread 123 is screwed into mating threaded region of electrode 116. Head 117 is then threaded over all thread 123. Thereafter, a wrench or socket may be inserted into aperture 125 to connect head 117 against electrode 116. One skilled in the art will recognize that various insulating region's may be provided between the various elements.

Figure 22:
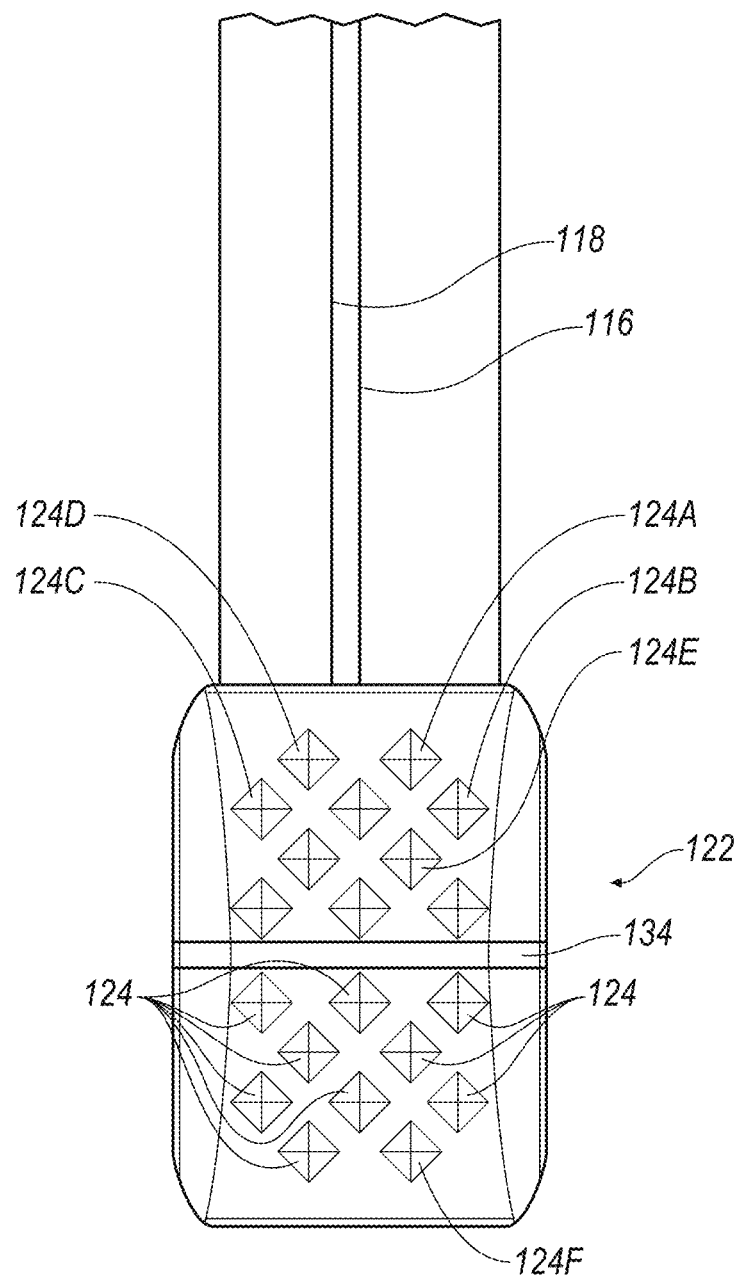
FIG. 22 is a plan view of a surgical tool according to an aspect of the invention.

Referring now to FIG. 21 and FIG. 22, another embodiment of the invention is shown and described. In FIG. 21, each of the teeth 124 is separated by a space 126. In the present embodiment, each of the teeth are depicted as being triangular and terminating at a point. Each of the spaces 126 provide separation between the teeth. Various functions and features of different teeth configuration will be understood from the description provided herein. In one embodiment, as depicted in FIG. 21 and FIG. 22, face 122 is shown having a boat configuration. Teeth 124 positioned at an outer region of face 122 are longer than teeth 124 position toward the center of face 122 such that the tips of each of the teeth 124 form a substantially flat plane. It will be understood, however, that face 122 may be flat in configuration and teeth 124 may have an equal length.

With continued reference to FIG. 22, another aspect of the present invention is shown and described. In FIG. 22 the plurality of teeth 124 may include differing electrical signals provided to each of the teeth 124. For example, electrical signals from conductor 118 may be provided to various teeth, for example, electrical signals may be provided to teeth 124A, 124B from conductor 118 while electrical signals from conductor 120 may be provided to other teeth such as 124D and 124F. Additionally, other conductors may also be provided such that each of the teeth 124 receives a different signal or various coordination of signals to achieve a desired surgical effect.

Figure 23:
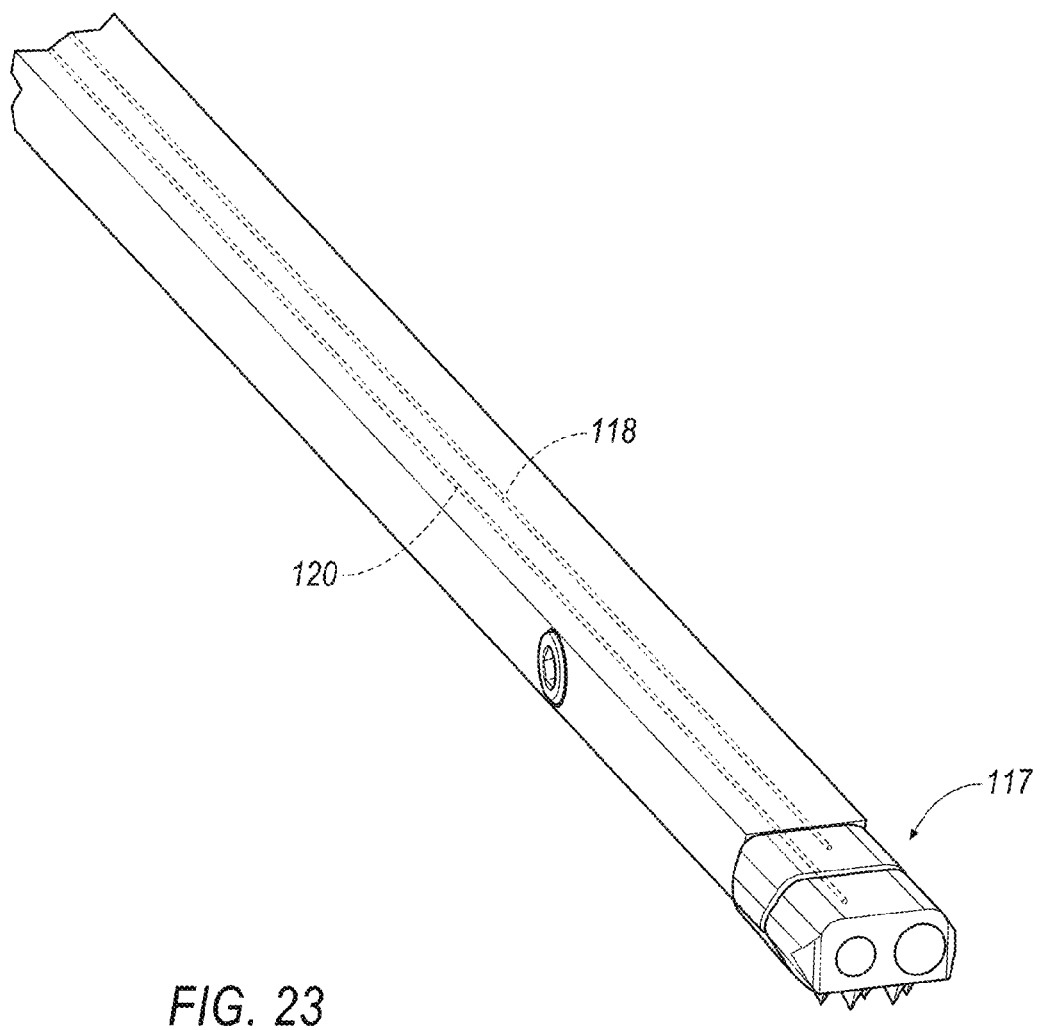
FIG. 23 is a perspective view of a surgical tool according to an aspect of the invention.
Figure 24:
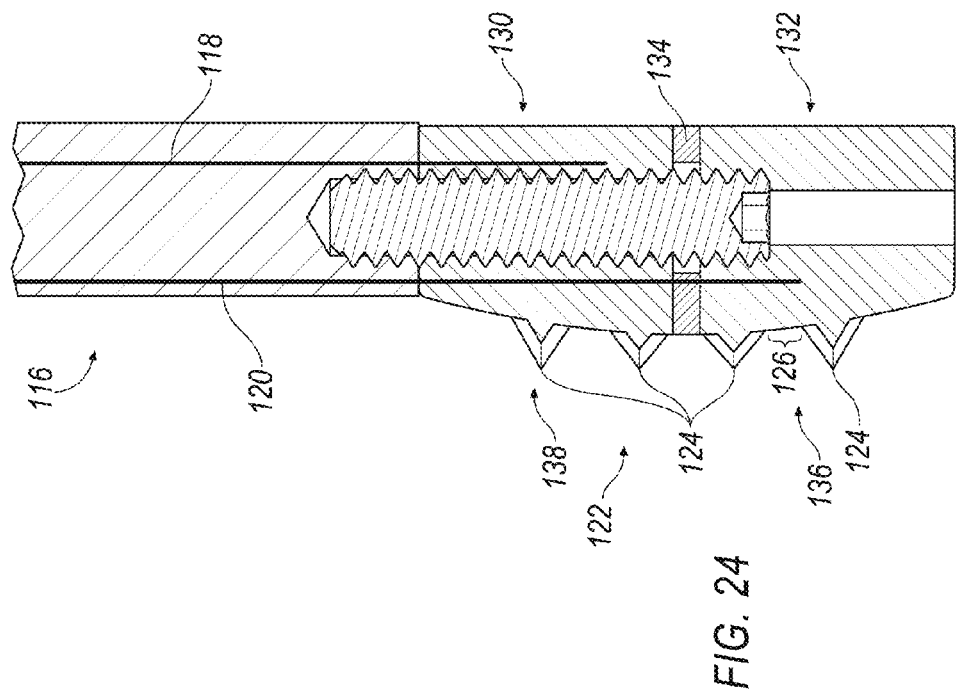
FIG. 24 is a side view of a surgical tool according to an aspect of the invention.

FIG. 23 and FIG. 24 show close-up views of that of FIG. 19. With respect to FIG. 24, head 117 is divided into first portion 130 and second portion 132 and separated by an insulator 134. Here, conductor 118 connects to first portion 130 while conductor 120 connects to second portion 132. Face 122 is likewise divided into first face 138 and second face 136. As depicted in the figure, the first portion 130 is axially (with respect to an axis of the instrument) rearward with respect to second portion 132. Thus, the head is generally rectangular and separated into a forward and a rearward region. As can be seen, conductor 118 provides an electrical signal to first face 138 and subsequently teeth 124 associated with first face 138. Likewise, conductor 120 provides a second electrical signal to second portion 132 and the second face 136 such that teeth 124 associated with second face 136 provide a second electrical signal. It will be noted that either the first or second electrical signal may be a ground. As a result, a bipolar configuration is provided such that electrical signals are provided between first face 138 and second face 136 through a patient.

Figure 25:
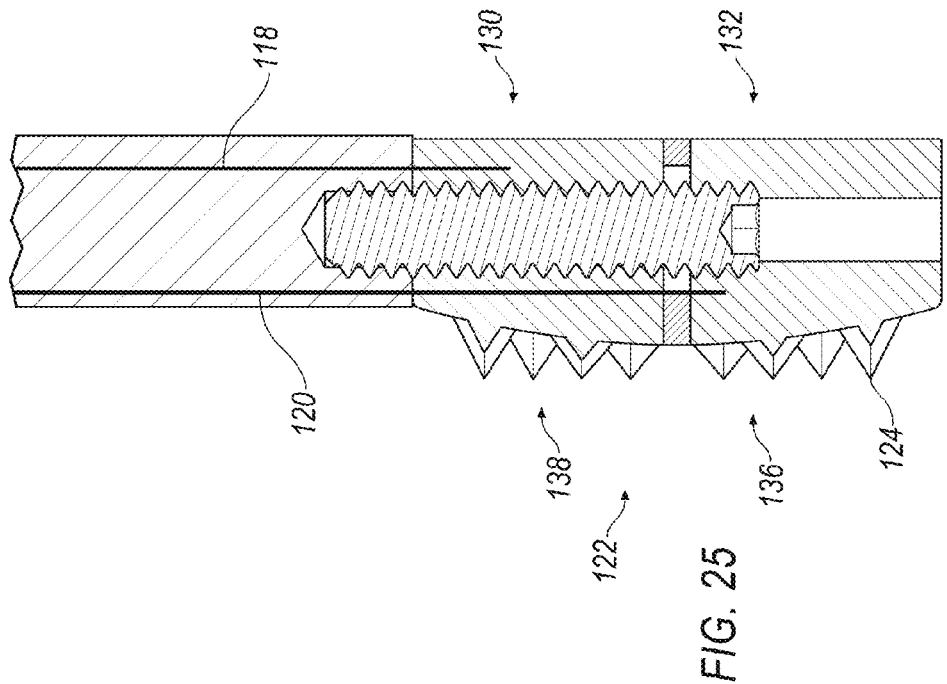
FIG. 25 is a side view of a surgical tool according to an aspect of the invention.

FIG. 24 shows another embodiment of the present invention where each of the teeth 124 are separated by a space 126. FIG. 25 shows another aspect of the present invention.

In operation, a surgical procedure such as that described in the incorporated patent, referenced above, may employ any aspect of the present invention. The head is placed in proximity to the area to be treated such that the electrical signal passes from the teeth through the area to be treated in the patient and either back through the surgical tool in a bipolar mode or through the patient in a monopolar mode.

In this specification, various preferred embodiments may have been described with reference to the accompanying drawings. It will, however, be evident that various modifications and changes may be made thereto, and additional embodiments may be implemented, without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. An electrosurgical device, comprising:
   a handle connectable to an RF generator;
   a head having a face connected at one end of the handle; and
   a plurality of teeth extending from the face;
   wherein at least one of the plurality of teeth as a first electrical charge;
   a second of the plurality of teeth has a second electrical charge; and
   a blade extending substantially perpendicular from the face with respect to a direction of the plurality of teeth;
   wherein the face includes a distal end located away from the handle and a proximal end located proximate the handle; and
   wherein the blade includes a front edge facing toward the distal end and a rear edge facing the proximal end.

2. The electrosurgical device according to claim 1, further comprising a side electrode positioned in the side electrode between the front edge and the rear edge.

3. The electrosurgical device according to claim 2, wherein:
   the front edge and the rear edge is a flat annular ring;
   the side electrode is a sphere; and
   the flat annular ring surrounds the sphere.

4. The electrosurgical device according to claim 1, wherein the front edge in the rear edge form a diamond shape.

* * * * *